United States Patent [19]
Ohmi

[11] Patent Number: 5,447,053
[45] Date of Patent: Sep. 5, 1995

[54] METHOD AND DEVICE FOR MEASURING QUANTITIES OF IMPURITIES IN SPECIAL GAS

[76] Inventor: Tadahiro Ohmi, 1-17-301, Komegabukuro 2-chome, Aoba-ku, Sendai-shi, Miyagi-ken 980, Japan

[21] Appl. No.: 150,142

[22] PCT Filed: May 13, 1992

[86] PCT No.: PCT/JP92/00605
§ 371 Date: Jan. 31, 1994
§ 102(e) Date: Jan. 31, 1994

[87] PCT Pub. No.: WO92/21966
PCT Pub. Date: Dec. 10, 1992

[30] Foreign Application Priority Data
May 30, 1991 [JP] Japan ................... 3-155880

[51] Int. Cl.$^6$ ............... G01D 18/00; G01N 13/04
[52] U.S. Cl. .......................... 73/31.03; 73/31.07
[58] Field of Search ........... 73/31.03, 31.02, 31.06, 73/31.07

[56] References Cited
U.S. PATENT DOCUMENTS
5,214,952 6/1993 Leggett et al. ............ 73/31.03 X FOREIGN PATENT DOCUMENTS
57-91451 6/1982 Japan .
1-20979 6/1989 Japan .
2-47549 2/1990 Japan .
353743 12/1992 Japan .................. 73/31.03

Primary Examiner—Hezron E. Williams
Assistant Examiner—J. David Wiggins
Attorney, Agent, or Firm—Young & Thompson

[57] ABSTRACT

A method and device for the quantitative measurement impurity in special gas at a level of ultra-high purity. After inert gas of ultra-high purity is supplied to a sample-gas pipe (14) through a purifier (1) (a first gas supply source), the inside of the sample-gas pipe (14) is baked by heating (22 to 24). Then, the inside of the sample gas (14) is kept in an atmosphere at a special temperature and a first and second changeover valves (9,10,16,17) are changed over so that a fixed quantity of special gas is supplied into the sample-gas pipe (14). Afterward, the special gas remaining in the sample-gas pipe (14) is discharged and the first and second changeover valves (9,10,16,17) are changed over so that impurities may be desorbed by baking the inside of the sample-gas pipe, and quantities of desorbed impurities are measured.

6 Claims, 2 Drawing Sheets

5,447,053

METHOD AND DEVICE FOR MEASURING QUANTITIES OF IMPURITIES IN SPECIAL GAS

TECHNOLOGICAL FIELD

The present invention relates to a measuring method for determining amounts of impurities contained in special gases (silane gas, disilane gas, and the like) for use in, for example, semiconductor manufacturing, in the case in which such a special gas is supplied through a pipe system, and furthermore relates to a device for use in such measurement.

BACKGROUND ART

Recently, the progress in the field of semiconductor manufacturing technology has been striking, and in particular, the demand for ultrafine structures and high levels of integration has become pressing; however, in conjunction with this, the necessity has arisen to maintain the environment of the manufacturing device in a state of ultrahigh purity (that is to say, purity on the level of parts per trillion). As a result, in the case in which sample gas of common gas (for example, argon gas, nitrogen gas, or the like) or special gas (for example, silane gas) having the necessary degree of ultrahigh purity for the manufacture of silicon substrates is supplied through a pipe system which serves as a gas flow path, it is necessary to determine the amount of impurities such as moisture and the like which are contained in the sample gas, on the level of parts per trillion.

Measuring methods for determining the impurity adsorption amount in common gases (argon gas, nitrogen gas, and the like), which were commonly employed, include the connection of a trace gas analyzer (atmospheric pressure ionization mass spectrometer) to the pipe end of a sample pipe through which this common gas is caused to flow, and measuring the amount of impurities flowing out of the pipe end of this sample pipe.

However, in the case in which such a special gas had corrosive or flammable characteristics, damage was done to the measurement system, or the handling of this gas presented difficulties, so that it was impossible to employ the measurement method which was used in the case of common gases. Accordingly, in the case of such special gasses, there was no method for confirming the relationship between impurity amounts and gas flow amounts, and the like, so that, in other words, only a rough estimate could be made, and this was insufficient for the purposes of the manufacture of semiconductors having the ultrafine structures discussed above.

The present invention solves the problems which were present in the conventional technology discussed above, and has as an object thereof to provide a device which is capable of conducting, easily, and on a level of parts per trillion, the measurement of impurity amounts and the like contained in special gasses which present difficulties in handling.

DISCLOSURE OF THE INVENTION

In order to attain the above object, the invention provides:
  a first step, wherein an inert gas having a high degree of purity is caused to flow through a sample pipe, an interior surface of which has been subjected to passivation processing;
  a second step, wherein baking is conducted within this sample pipe until an ultrahigh purity level is attained;
  a third step, wherein an atmosphere within the sample pipe is set to a predetermined temperature;
  a fourth step, wherein a predetermined amount of a special gas is caused to flow within the sample pipe;
  a fifth step, wherein an amount of the special gas remaining within the sample pipe is removed;
  a sixth step, wherein baking is conducted within the sample pipe until an ultrahigh level of purity is attained; and
  a seventh step, wherein the amount of impurities desorbed from the inner surface of the sample pipe by means of the baking of the sixth process is measured.

The invention further provides:
  a first gas supply source for supplying an inert gas having an ultrahigh degree of purity;
  a second gas supply source for supplying a special gas through the medium of a gas flow control meter;
  a first change-over valve, which is capable of selectively changing the flow of the inert gas or the special gas;
  a second change-over valve, which is connected to one end opening of the sample pipe, another end opening of which is connected to the first change-over valve, and which is capable of bidirectional flow change-over;
  a support means for supporting the sample pipe;
  an exhaust means connected to one side of the second change-over valve;
  a trace gas analyzer connected to another side of the second change-over valve; and
  a heating means capable of controlling the temperature within the sampling pipe at a freely selected temperature.

In this case, a construction is preferable in which the inert gases or special gases are caused to pass through at least a gas connection part, which regulates discharged gases so that the purity level of each gas does not decline.

Furthermore it is preferable that the trace gas analyzer described above comprise an atmospheric pressure ionization mass spectrometer.

FUNCTION

First, by causing an inert gas having a ultrahigh degree of purity (that is to say, argon gas or the like, having an impurity concentration on the level of parts per trillion) to flow through a sample pipe, the inner surface of which has been subjected to passivation processing, the interior of this sample pipe is placed in an atmosphere having a high degree of purity. Next, a heating mechanism is engaged, and baking is conducted at a predetermined high temperature so that the atmosphere within the sample pipe attains an ultrahigh level of purity (a background level). Next, the interior of the sample pipe is cooled, and the heating mechanism described above, which heats the atmosphere to a predetermined temperature, is controlled. After this, a fixed amount (a fixed flow amount within a fixed time period) of a special gas (silane gas, or the like) having a predetermined impurity concentration level is caused to flow through the interior of the sample pipe. Next, the flow of this special gas is terminated, and the sample gas is discharged from within the sample pipe in as short a period as possible by means of an exhaust mechanism. After this, baking is conducted by means of the heating mechanism described above, so that the interior of the sample pipe reaches the above-described ultrahigh purity level, and the quantities of impurities desorbing from the sample pipe during this period are measured.

DESCRIPTION OF REFERENCES

| (Description of References) | |
| --- | --- |
| 1 | Gas purifier (first gas supply source) |
| 4 | Gas tank (second gas supply source) |
| 6 | Gas flow controller |
| 9, 10, 11 | Third, fourth, and fifth valves (first change-over valve) |
| 14 | Sample pipe |
| 16, 17, 20 | Seventh, eighth and tenth valves (second change-over valve) |
| 13, 15 | First and second couplings (support mechanisms) |
| 28 | APIMS (trace gas analyzer) |
| 22, 23, 24 | Heaters (heating mechanisms) |

BEST MODE FOR CARRYING OUT THE INVENTION

Figure 1:
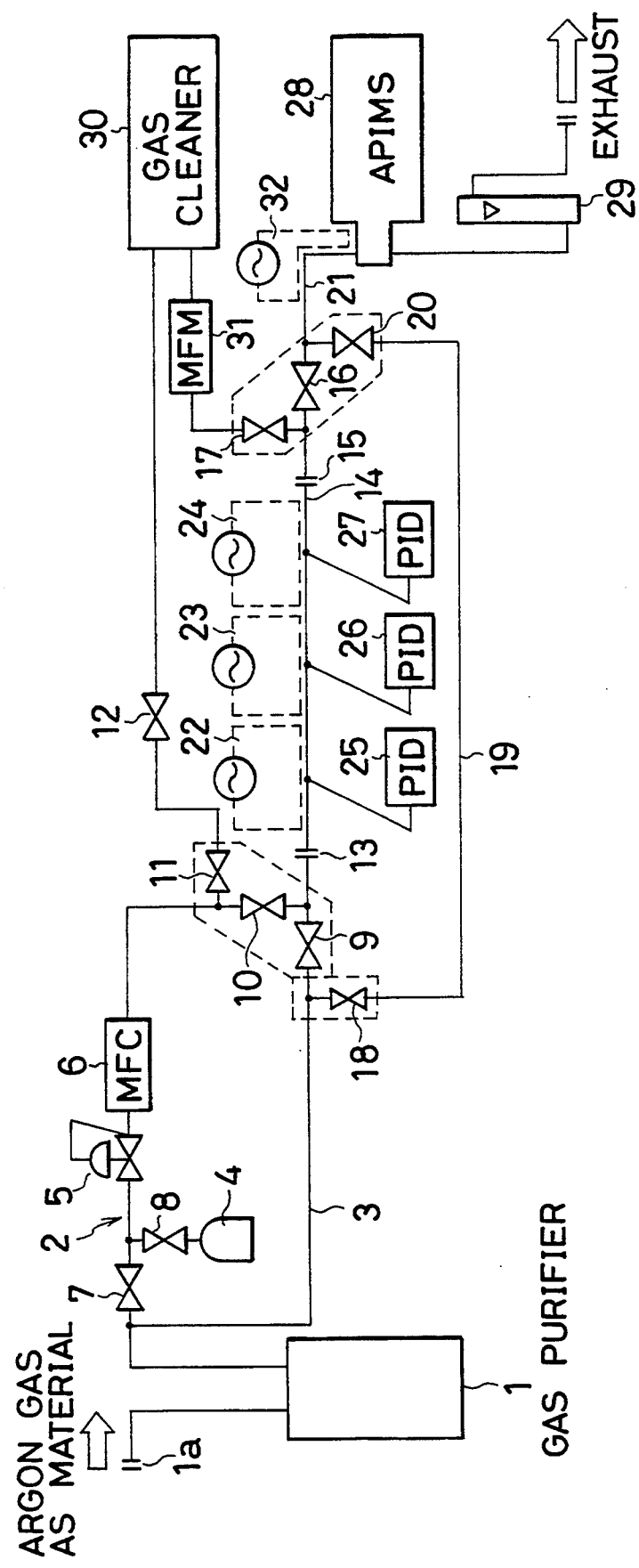
FIG. 1 is a gas flow diagram showing an embodiment of a device employed in a measurement method for impurity quantities in accordance with the present invention.

FIG. 1 shows a embodiment of a device for the execution of a measurement method in accordance with the present invention. As shown in the diagram, for example, a supply source (not depicted in the figure) or a source gas, which is an inert gas such as argon or the like, is connected through the medium of gas coupling 1a to the gas inlet side of purifier 1 comprising the first gas supply source, and first and second gas supply lines 2 and 3 are connected to the gas output side thereof. A special gas (silane gas) gas tank 4, comprising the second gas supply source, a regulator 5, and a gas flow controller (MFC) 6, are connected to the first gas supply line 2 in that order from the upstream side thereof. Along the first gas supply line 2, a first valve 7 is provided at an upstream position from regulator 5, and gas tank 4 is connected to the downstream side of this first valve 7, that is to say, to the first gas supply line 2, through the medium of second valve 8.

Furthermore, a third valve 9 is provided on the second gas supply line 3, and, on the downstream side of MFC 6, a fourth valve 10 and a fifth valve 11 are provided in a branching manner.

Argon gas of ultrahigh purity is provided from purifier 1 and gas tank 6 is filled with a special gas of ultrahigh purity at a predetermined concentration (for example, a gas in which 5% of silane gas is mixed with 95% of hydrogen gas).

The third, fourth, and fifth valves 9, 10, and 11 comprise the integrated first change-over valve; the opening and closing of the third and fifth valves 9 and 11, and of the fourth valve 10, is conducted exclusively. Furthermore, the third and fourth valves 9 and 10 are connected to one end opening of sample gas pipe 14 through the medium of first coupling 13, which is a support mechanism, and the other end opening of sample gas pipe 14 is connected to the seventh and eighth valves 16 and 17, comprising the second change-over valve, through the medium of the second coupling 15, which is another support mechanism.

A ninth valve 18 is connected to the second gas supply line 3; this ninth valve 18 is connected to a tenth valve 20, comprising the second change-over valve, through the medium of bypass line 19, and the convergence part of the downstream side of tenth valve 20 and the downstream side of seventh valve 16 is connected to junction pipe 21.

Furthermore, an appropriate number of heaters 22-24 are provided along the longitudinal direction of sample gas pipe 14 by zone, and temperature detectors 25-27 are provided corresponding to each zone. Each heater 22-24 is provided so as to be capable of controlling, with a high degree of accuracy, the temperature of the several allocated zones of sample gas pipe 14, based on the output of temperature detectors 25-27.

An atmospheric pressure ionization mass spectrometer (APIMS) 28 is connected to junction pipe 21 as a trace gas analyzer, and an exhaust mechanism is connected to the detection portion of APIMS 28 through the medium of flow meter 29.

A cleaning mechanism 30 is connected to sixth valve 12, and furthermore, an eighth valve 17 is connected to cleaning mechanism 30 through the medium of gas flow meter (MFM) 31, while a small heater 32 is connected to junction pipe 21. Furthermore, parts which are in contact with gas, such as the first and second change-over valves, and the gas junction, are constructed completely of metal, and discharge gasses are controlled so that the purity of the argon gas or the silane gas passing therethrough is not lowered.

Next, a measurement method in accordance with the present embodiment and utilizing the above construction will be explained.

First, sample gas pipe 14 has dimensions such that, for example, the diameter thereof is ¼ inch and the length thereof is 2 meters, and is made of stainless steel, and furthermore, the inner surface thereof has been subjected to passivation processing, that is to say, electropolishing, and an oxide film has been formed thereon, and this pipe is affixed between couplings 13 and 15.

Next, first valve 7 is opened, second valve 8 is closed, and the third, fifth, sixth, and seventh valves 9, 11, 12, and 16 are opened, while the fourth, eighth, ninth, and tenth valves 10, 17, 18, and 20 are closed. That is to say, argon gas of ultrahigh purity is caused to flow into first and second gas supply lines 2 and 3; the argon gas flowing in the first gas supply line 2 is caused to flow into cleaning mechanism 30, while the argon gas flowing in the second gas supply line 3 purges the interior of sample gas pipe 14. At this time, it is possible to confirm whether or not argon gas is flowing in sample gas pipe 14 by means of flow meter 29, and furthermore, it is possible to measure the purity and the like of the argon gas at this time by means of APIMS 28.

Next, heaters 22, 23, and 24 are controlled, and the interior of sample gas pipe 14 is set to a high temperature atmosphere of, for example, 450° C.; that is to say, baking is conducted.

Next, from the opened and closed state of each valve described above, the first valve 7 is closed, while the second valve 8 is opened. By means of this, silane gas is caused to flow into the first gas supply line 2 from gas supply tank 4; this gas is set to a fixed moisture concentration (for example, 10 ppb) and is caused to flow at a predetermined flow amount (for example, 1.2 liter/min)

by means of regulator 5, and flows in the direction of cleaning mechanism 30.

Next, seventh valve 16 is closed, while eighth, ninth, and tenth valves 17, 18, and 20 are opened. By means of this, a purge of bypass line 19 is conducted using argon gas.

Next, heaters 22, 23, and 24 are controlled, the interior of sample gas pipe 14, which was subjected to baking, is allowed to cool, and is maintained at a predetermined temperature (for example, 25° C.).

When the interior of sample gas pipe 14 is maintained at a fixed temperature, the fourth valve 10 is opened, while the third, fifth, and sixth valves 9, 11, and 12 are closed. By means of this, silane gas is caused to flow at the above-described flow amount into sample gas pipe 14; however, as a result of this, the adsorption of the moisture contained in the silane gas to the inner walls of sample gas pipe 14 begins. If the time at which silane gas flow is initiated, and the display value of MFC 6, are recorded, it is possible to estimate the amount of silane gas flowing into the interior of sample gas pipe 14.

Next, the fourth valve 10 is closed, while the third, fifth, and sixth valves 9, 11, and 12 are opened. As a result, the flow of the silane gas into sample gas pipe 14 is halted, the silane gas remaining within sample gas pipe 14 is discharged in a short period of time by means of argon gas from purifier 1, and this gas is discharged in a form in which it has been diluted below a predetermined concentration by means of cleaning mechanism 29. It is readily possible to determine whether or not the silane gas has been discharged from within the sample gas pipe 14, and to determine the discharged amount, by observation of MFM 30. The discharge amount of the silane gas is necessary for adjustments when the actual value of the moisture contained therein is determined.

Next, the seventh valve 16 is opened, while the eighth, ninth, and tenth valves 17, 18, and 20 are closed. By means of this, only an argon gas of ultrahigh purity is caused to flow into sample gas pipe 14, and in this state, heaters 22, 23, and 24 are put into operation, and so that the interior of sample gas pipe 14 reaches the background purity level described above, baking is conducted. It is possible to determine whether or not this baking has been completed, and to determine the amount of moisture desorbing from the inner walls of the sample gas pipe 14 during the period until the completion of baking, by means of APIMS 28.

By means of controlling small heater 23, it is possible to maintain the interior of junction pipe 21 at a predetermined high temperature, and furthermore, it is possible to determine the gas flow state from sample gas pipe 14 by means of flow duration meter 29.

Next, first valve 7 is opened, and second valve 8 is closed, and at this time, a purge is conduced of the first and second gas supply lines 2 and 3 by means of argon gas, thus returning the supply lines to their initial state.

After this, the order of operations described above is repeated, and the moisture amount within the silane gas in cases in which the interior of sample gas pipe 14 is set to a differing atmospheric temperature (for example, 40° C., 60° C., 80° C., or the like) is measured.

Figure 2:
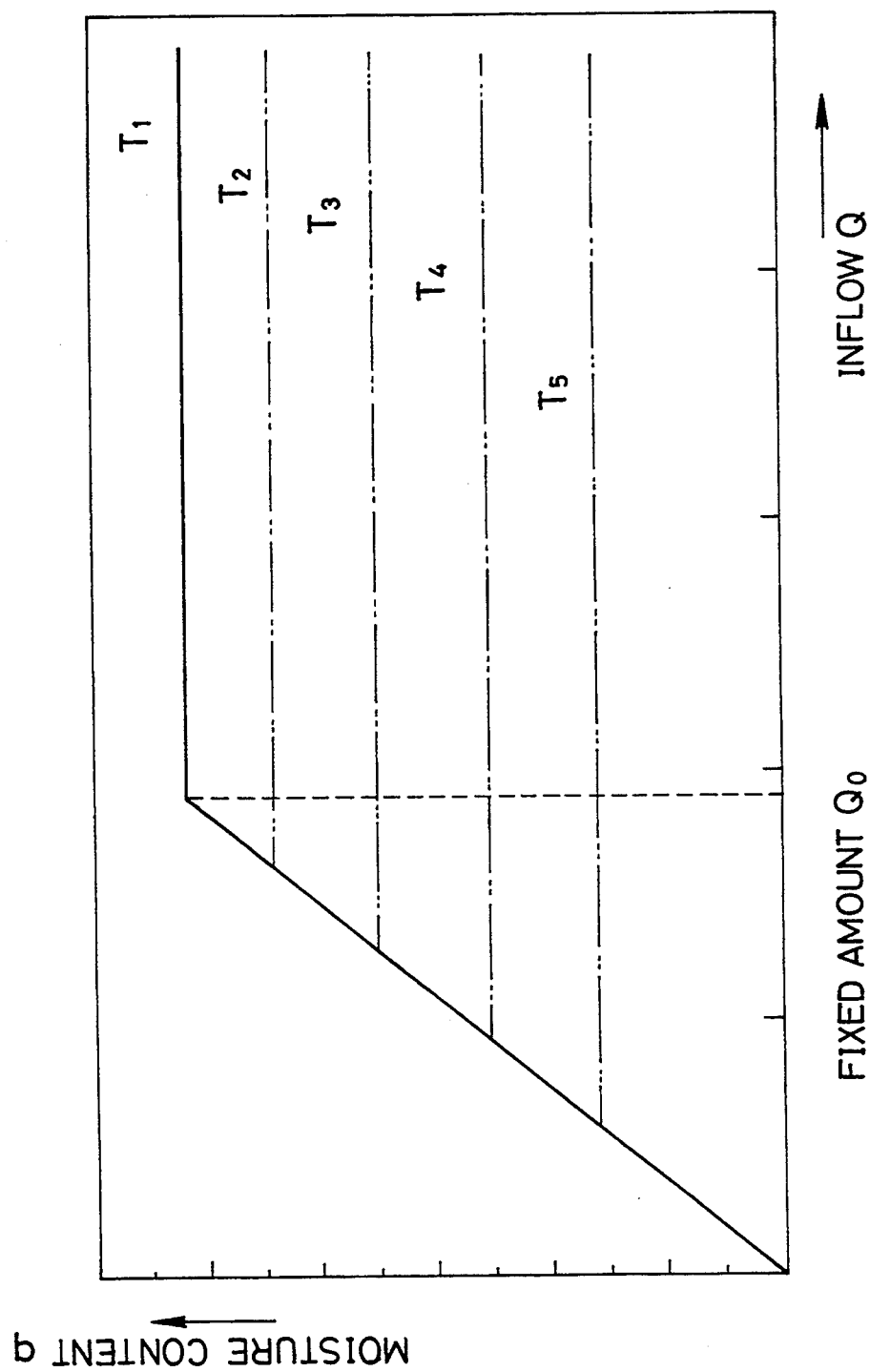
FIG. 2 is a graph showing the results of measurements conducted by the device shown in FIG. 1.

FIG. 2 shows the results of measurements of moisture amounts contained in the case in which a fixed flow amount (0.5 liter/min) of silane gas having a predetermined concentration was caused to flow through sample gas pipe 14. As can be understood from the diagram, in the region in which the inflow Q of silane gas is small, the inflow Q and the moisture content q are in a proportional relationship, while when inflow Q exceeds a fixed amount $Q_o$, as a result of the saturation of moisture adsorption to the inner wall of sample gas pipe 14, the moisture content also becomes saturated.

As shown by the extrapolated lines in the diagram (straight lines $T_1, T_2, T_3, \ldots$) as the temperature within sample gas pipe 14 is raised in the order $T_1, T_2, T_3, \ldots$, the saturation value of the moisture content decreases.

I claim:

1. A method for measuring impurities in a special gas in which the amount of impurities is to be measured, wherein are performed:
    a first step, wherein an inert gas having a high degree of purity is caused to flow through a sample pipe, an interior surface of which has been subjected to passivation processing;
    a second step, wherein baking of said sample pipe is conducted until an ultrahigh purity level of the atmosphere within said sample pipe is attained;
    a third step, wherein an atmosphere within said sample pipe is set to a predetermined temperature;
    a fourth step, wherein a predetermined amount of a said special gas is caused to flow within said sample pipe;
    a fifth step, wherein an amount of said special gas remaining in the atmosphere within said sample pipe is removed;
    a sixth step, wherein baking is conducted within said sample pipe until said ultrahigh level of purity of the atmosphere within said sample pipe is attained; and
    a seventh step, wherein an amount of impurities desorbed from an inner surface of said sample pipe by said baking of said sixth step is measured.

2. A method for measuring impurities in special gas in accordance with claim 1, wherein said special gas is silane gas.

3. A method for measuring impurities in special gas in accordance with claim 1, wherein said inert gas is argon gas.

4. A device for measuring impurities in special gas, wherein are provided:
    a first gas supply source for supplying an inert gas having an ultrahigh degree of purity;
    a second gas supply source for supplying a special gas in which the amount of impurities is to be measured, through a flow path which includes the medium of a gas flow control meter;
    a first change-over valve, which is capable of selectively changing a flow of said inert gas or said special gas;
    a second change-over valve, which is connected to one end opening of a sample pipe, another end opening of which is connected to said first change-over valve, and which is capable of bidirectional flow change-over;
    a support means for supporting said sample pipe;
    an exhaust means connected to one side of said second change-over valve;
    a trace gas analyzer connected to another side of said second change-over valve; and
    a heating means capable of controlling a temperature within said sample pipe at a freely selected value.

5. A device for measuring impurities in special gas in accordance with claim 4, wherein said inert gas and said special gas pass through a gas connection part and second change-over valves, associated with one of the first change-over discharge gases of which are regulated so that a purity level of each gas is at least not lowered.

6. A device for measuring impurities in special gas in accordance with claim 4, wherein said trace gas analyzer comprises an atmospheric pressure ionization mass spectrometer.

* * * * *